Figure 1:
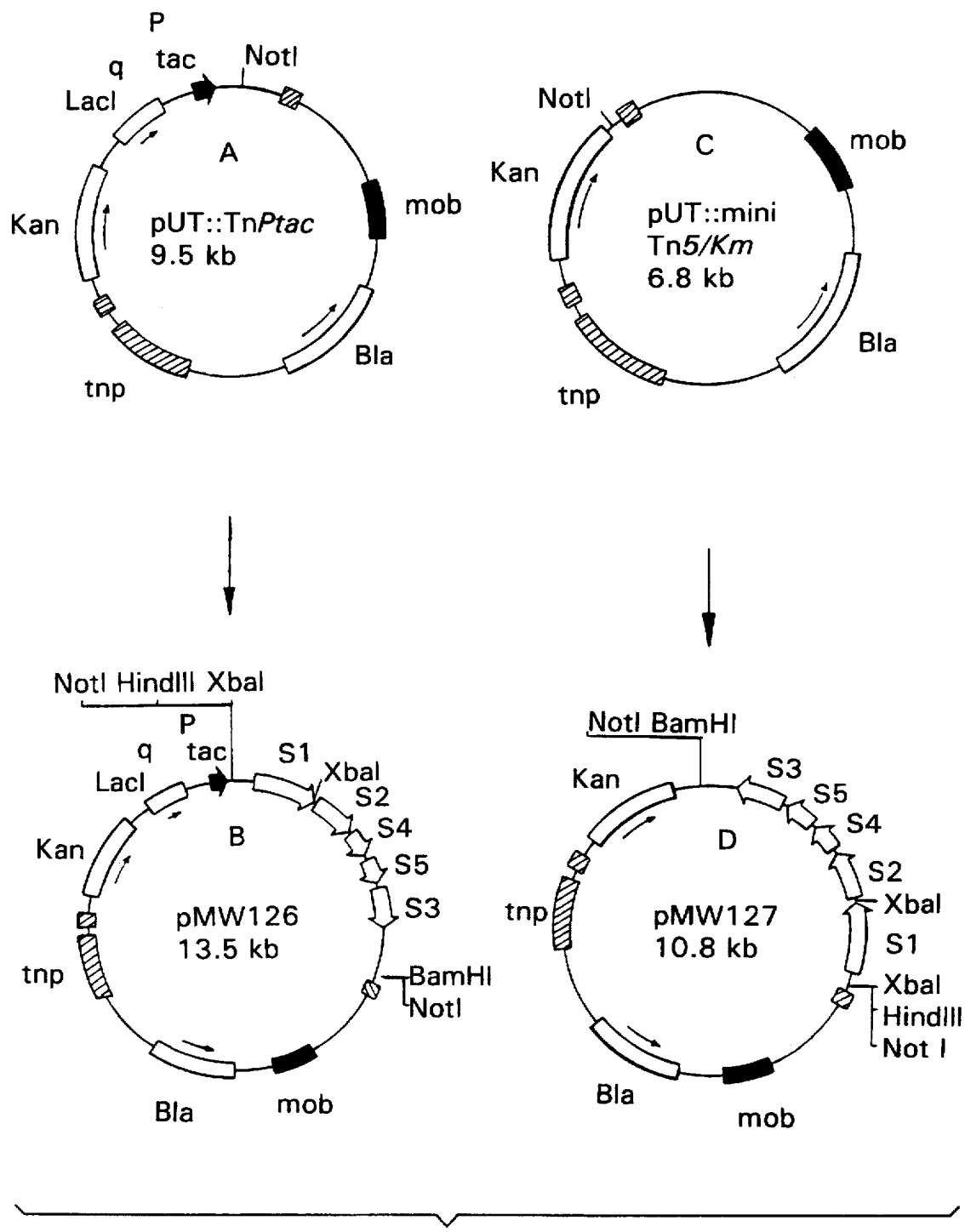

United States Patent [19]

Walker et al.

[11] Patent Number: 5,705,361
[45] Date of Patent: Jan. 6, 1998

[54] HYBRID TRANSPOSON WITH PT OPERON, PLASMIDS AND BACTERIAL STRAINS THEREFOR

[75] Inventors: Mark Walker; Kenneth Timmis, both of Brunswick, Germany

[73] Assignee: Gesellschaft fur Biotechnologische Forschung mbH GBF, Brunswick, Germany

[21] Appl. No.: 137,139

[22] PCT Filed: Apr. 24, 1992

[86] PCT No.: PCT/EP92/00910

§ 371 Date: Oct. 21, 1993

§ 102(e) Date: Oct. 21, 1993

[87] PCT Pub. No.: WO92/19750

PCT Pub. Date: Nov. 12, 1992

[30] Foreign Application Priority Data

Apr. 24, 1991 [DE] Germany .................. 41 13 385.4

[51] Int. Cl.⁶ .................. C12P 21/02; C12N 1/20; C12N 15/74

[52] U.S. Cl. .................. 435/69.3; 435/252.3; 435/320.1
[58] Field of Search .................. 435/320.1, 252.3, 435/172.3, 69.3; 424/92

[56] References Cited

U.S. PATENT DOCUMENTS 4,883,761  11/1989  Keith et al. .................. 435/320.1

OTHER PUBLICATIONS

Walker et al., *Infection and Immunity*, vol. 59, Nov. 1991, pp. 4238–4248.

Herrero et al., *V. Bacteriol.*, vol. 172, Nov. 1990, pp. 6557–6567.

Bloom, *Rev. Infect. Diseases*, vol. 11, Supplement 2, 1989, pp. 5460–5466.

Knapp et al., vol. 170, *J. Bacteriol.*, 1988, pp. 5059–5066.

*Primary Examiner*—James S. Ketter
*Attorney, Agent, or Firm*—Kane, Dalsimer, Sullivan, Kurucz, Levy, Eisele and Richard

[57] ABSTRACT

The invention relates to a hybrid transposon having a PT operon, to plasmids and to bacterial strains (hosts) therefor.

12 Claims, 4 Drawing Sheets

HYBRID TRANSPOSON WITH PT OPERON, PLASMIDS AND BACTERIAL STRAINS THEREFOR

BACKGROUND OF THE INVENTION

1. Field of the Invention

The invention relates to a plasmid for bacterial expression of pertussis toxin, useful in vaccine preparation.

2. Brief Description of Related Art

Increasing concern regarding the side-effects associated with immunization using whole cell preparations of *B. pertussis* has led to a decreasing acceptability of vaccines against whooping cough. This has in turn resulted in an increase in the incidence of the disease. It is imperative that an effective, nonreactogenic vaccine of high acceptability be developed. Several potentially protective antigens are candidates for inclusion in a purified multi-component vaccine, including toxins, such as pertussis toxin (PT) and adenylate cyclase, and also several cell surface or secreted antigens like filamentous haemagglutinin and serotype-specific fimbriae (Robinson, A., et al. 1985. Pertussis vaccine: present status and future prospects. Vaccine 3:11–22; and Robinson, A., and L. A. E. Ashworth. 1988. Acellular and defined-component vaccines against pertussis, p. 399–417. In A. C. Wardlaw, and R. Parton (ed.). Pathogenesis and Immunity in Pertussis. John Wiley and Sons, Chichester). However, *Bordetella pertussis* is a nutritionally fastidious microorganism. Purification of antigens obtained directly from *B. pertussis* is hampered by antigenic variation controlled by the bvg-positive regulatory locus (Gross, R., and R. Rappuoli. 1988. Positive regulation of pertussis toxin expression. Proc. Natl. Acad. Sci. 85:3913–3917; Knapp, S., and J. J. Mekalanos. 1988. Two trans-acting regulatory genes (vir and mod) control antigenic modulation in *Bordetella pertussis*. J. Bacterial. 170:5059–5066; and Weiss, A. A., and S. Falkow. 1984. Genetic analysis of phase change in *Bordetella pertussis*. Infect. Immun. 43:263–269), poor bacterial growth rates, low yields, and the presence of reactogenic contaminants. To overcome those problems, attempts have been made to obtain expression of recombinant antigens in *E. coli* using strong transcriptional and translational signals. The five genes encoding PT have been expressed independently of one another in *E. coli* under the control of the lambda $P_L$ promoter (Burnette, W. N., et al. 1988. Direct expression of *Bordetella pertussis* toxin subunits to high levels in *Escherichia coli*. Biotechnol. 6:699–706). The serotype 2 fimbrial sub-unit has also been expressed with the aid of the lambda $P_L$ and $P_R$ promoters (Walker, M. J., et al. 1990. engineering upstream transcriptional and translational signals of *Bordetella pertussis* serotype 2 fimbrial subunit protein for efficient expression in *Escherichia coli:* in vitro auto-assembly of the expressed product into filamentous structures. Mol. Microbiol. 4.39–47). In both cases the recombinant proteins failed to assemble into products that were immunologically identical with the native antigens. Pertussis holotoxin can be produced in recombinant *B. parapertussis* and *B. bronchiseptica* strains under the control of the original *B. pertussis* promoter. However, the level of expression detected was less than that for wild-type *B. pertussis* and the expression was also subject to modulation and bvg-controlled phase variation. Recombinant broad-host-range plasmids carrying the PT operon were also extremely unstable, being subject to both plasmid loss and gene deletions (Locht, C., et al. 1986. Molecular cloning of pertussis toxin genes. Nucl. Acids Res. 14:3251–3261).

The invention described in the following is based on the above-mentioned prior art and on the problem of making pertussis toxin a central component of new-generation vaccines.

SUMMARY OF THE INVENTION

Thus, one embodiment of the invention relates to a hybrid transposon that can be produced by inserting a pertussis toxin operon (PT operon) between the inverted repeats of a transposon.

That hybrid transposon is accordingly promoterless. For the purpose of expression, it is to be under the control of a native promoter after chromosomal integration.

The hybrid transposon according to the invention can be produced by using the inverted repeats in unshortened or shortened form, the shortened inverted repeats permitting a further transposition.

The hybrid transposon according to the invention may be characterised in that it is a mini-transposon.

BRIEF DESCRIPTION OF THE DRAWINGS

FIG. 1 shows the construction of a suicide vector with mini-transposons for PT expression under the control of the tac promoter (pMW126) and as transcriptional fusions with native promoters (pMW127).

FIG. 2, panels A–B, shows the Southern hybridization analysis of *B. bronchiseptica* ATCC 10580 containing PT-expressing transposons.

FIG. 3, panels A–B, shows the analysis of PT expression by *B. bronchiseptica* ATCC 10580 (Lane 1) containing TnPtacPT (Lane 2) and TnfusPT (Lane 3), *B. pertussis* Tohama (Lane 4) and purified PT (Lane 5) also being shown.

FIG. 4, panels A–G, characterizes the recombinant PT.

DETAILED DESCRIPTION OF THE PREFERRED EMBODIMENTS OF THE INVENTION

The hybrid transposon according to the invention can also be produced by starting from Tn5 and taking, for example, inverted repeats each having a length of approximately 19 base pairs, such as, for example, for TnPtacPT or TnfusPT.

The hybrid transposon according to the invention can also be produced by incorporating a PT operon which is a wild-type PT operon or a PT operon that encodes a pertussis toxin modification that can be used for combating whooping cough.

The hybrid transposon according to the invention may also be characterised in that the hybrid transposon comprises a resistance gene, for example the kanamycin resistance gene ($Km^r$=Kan).

The resistance gene may be arranged in the same direction of reading as or in the opposite direction of reading to the PT operon.

A further embodiment of the invention relates to a plasmid characterised by a hybrid transposon according to the invention.

Finally, one embodiment of the invention relates to a bacterial strain (a), such as *Bordetella pertussis, Bordetella parapertussis* or *Bordetella bronchiseptica*, for example ATCC 10580, having a vector (plasmid) according to the invention or (b) obtainable by incorporating a PT operon by means of a hybrid transposon according to the invention or a vector (plasmid) according to the invention into *Bordetella pertussis, Bordetella parapertussis* or *Bordetella bronchiseptica*, for example ATCC 10580.

The bacterial strain may be a bvg-negative strain.

According to a special embodiment of the invention, mini-transposons are provided for the constitutive and inducible expression of PT in bvg-negative strains of B. bronchiseptica as a result of which a stable high-level expression of PT in bvg-negative B. bronchiseptica strains is rendered possible. The use of such strains offers a number of advantages for the production of PT for vaccination purposes, such as fast bacterial growth rates, high yields and the absence of other bvg-controlled virulence determinants which play a role in the discussed side-effects of PT preparations and pertussis vaccines.

In this connection it should be pointed out that methods for the genetic detoxification of PT have recently been developed by several groups (Kimura, A., et al. 1990. Pertussis toxin analog with reduced enzymatic and biological activities is a protective antigen. Infect. Immun. 58:3337-3347; and Nencioni, L., et al. 1990. Characterization of genetically inactivated pertussis toxin mutants: candidates for a new vaccine against whooping cough. Infect. Immun. 58:1308-1315). However, those methods rely on the purification of detoxified PT from B. pertussis. The production of pertussis holotoxin by means of bvg-negative strains of B. bronchiseptica in combination with methods for the genetic detoxification of PT will lead to a vaccine component of high purity and low reactogenicity.

The invention is explained in more detail hereinafter using Figures and a Table.

Plasmid pTX42 (11; see also U.S. Pat. No. 4,883,761; ATCC 67046) containing the genetic information for encoding the five pertussis toxin sub-units was used as the starting material. In addition, the known construction of mini-transposons (De Lorenzo, V., et al. 1990. Mini-Tn5 transposon derivatives for insertion mutagenesis, promotor probing, and chromosomal insertion of cloned DNA in Gram-negative eubacteria. J. Bacterial. 172:6568–6572; and Herrero, M., et al. (1990) Transposon vectors containing non-antibiotic resistance selection markers for cloning and stable chromosomal insertion of foreign genes in Gram-negative bacteria. J. Bacterial. 172:6557–6567) was used as a basis for the expression in bvg-negative strains of B. bronchiseptica ATCC 10580. Since, however, the transposase is lost with the suicide delivery vehicle, the mini-transposon system can undergo only a single transposition step, so that further transposition- and transposon-mediated deletions and rearrangements do not occur.

EXAMPLE 1

Construction of the mini-hybrid transposons TnPtacPT and TnfusPT and their integration into the chromosome of B. bronchiseptica ATCC 10580

Figure 2:
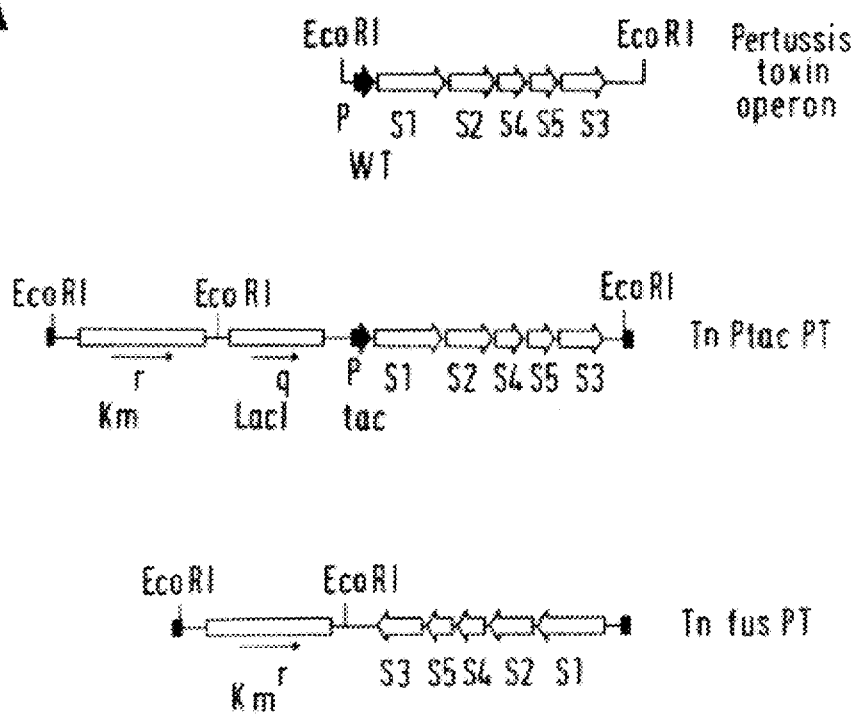
Figure 2:
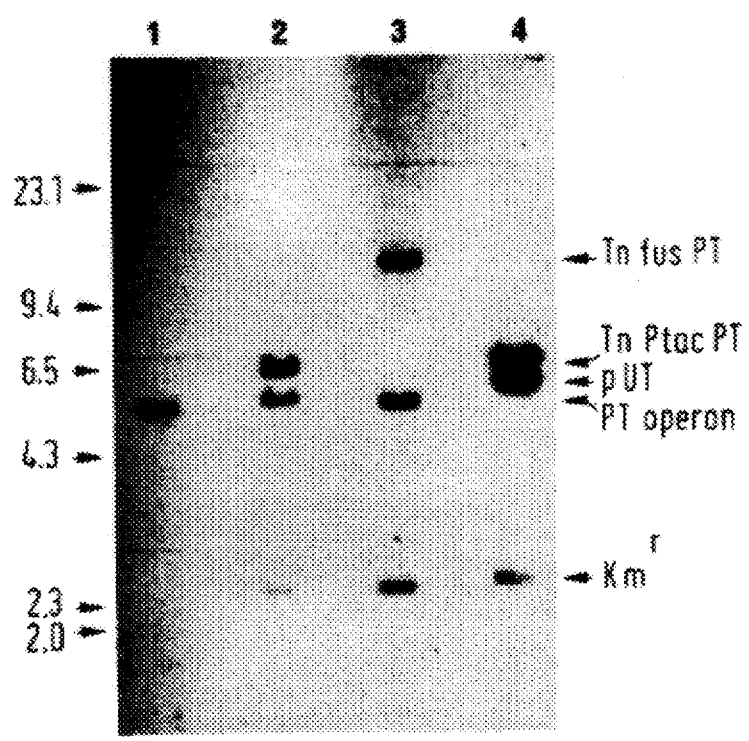
Figure 3:
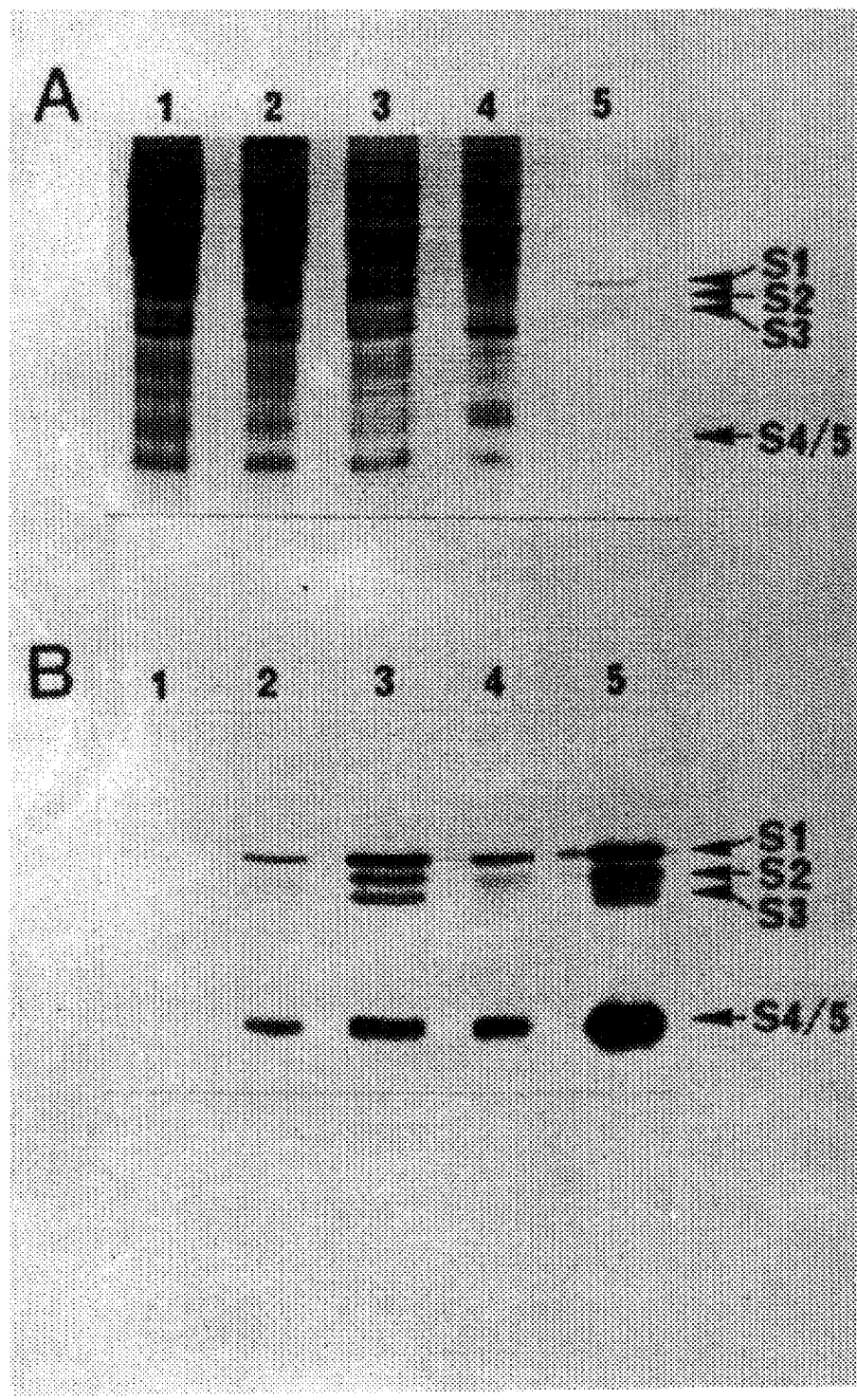

Mini-transposons containing the PT operon were constructed in an attempt to overexpress PT in bvg-negative B. bronchiseptica strain ATCC 10580. The PT operon was cloned using polymerase chain reaction techniques into the pUT::miniTn5 chromosomal integration system. The promoterless PT operon was (without $P_{WT}$)
on the one hand cloned in the same orientation as the tac promoter (Ptac) of pUT::TnPtac to form pMW126 (TnPtacPT) and
on the other hand in the opposite orientation in pUT::miniTn5/Km to produce pMW127 (TnfusPT) (FIG. 1). After mobilisation of pMW126 and pMW127 to ATCC 10580, transconjugates were screened for PT production (colony immunoblots; Western blots) and loss of the suicide vector by Southern hybridisation (FIG. 2). Selected transconjugants were designated ATCC 10580::TnPtacPT and ATCC 10580::TnfusPT. When compared with PT expression by B. pertussis, TnPtac provided IPTG-inducible PT expression at a lower level. On the other hand, TnfusPT provided substantially higher levels of PT expression than B. pertussis after transcriptional fusion between a native promoter (of B. bronchiseptica) and the promoterless PT operon (FIG. 3). Compared with the broad-host-range plasmid pDSK519 (Keen, N. T., et al. 1988. Improved broad-host-range plasmids for DNA cloning in Gram-negative bacteria. Gene 70:191–197) containing the PT operon under the control of the lac promoter (pMW124), the mini-transposon system was very stable with no detected loss after 60 generations without antibiotic selection. In this connection, reference should be made to Table 1.

TABLE 1

Stability of PT expression by B. bronchiseptica ATCC 10580 pMW124 and ATCC 10580::TnfusPT after 60 generations without antibiotic selection.

| Bacterial strain | CFU/ml[a] | | PT (%) without Selection[b] | linkage of PT with Km$^r$ (%)[c] |
|---|---|---|---|---|
| | Cp$^r$ | Cp$^r$Km$^r$ | | |
| ATCC 10580 pMW124 | 2.1 × 10$^9$ | 3.0 × 10$^5$ | <1% | 100% |
| ATCC 10580::TnfusPT | 3.0 × 10$^9$ | 2.9 × 10$^9$ | 100% | 100% |

[a]after 60 generations without kanamycin selection colony forming units (CFU) per ml of culture were determined by selection either with cephalexin (Cp) alone or in combination with kanamycin (Kn).
[b]100 Cp$^r$ colonies were screened for PT production by colony immunoblotting.
[c]100 Cp$^r$ Km$^r$ colonies were screened for PT production by colony immunoblotting.

Figure 4:
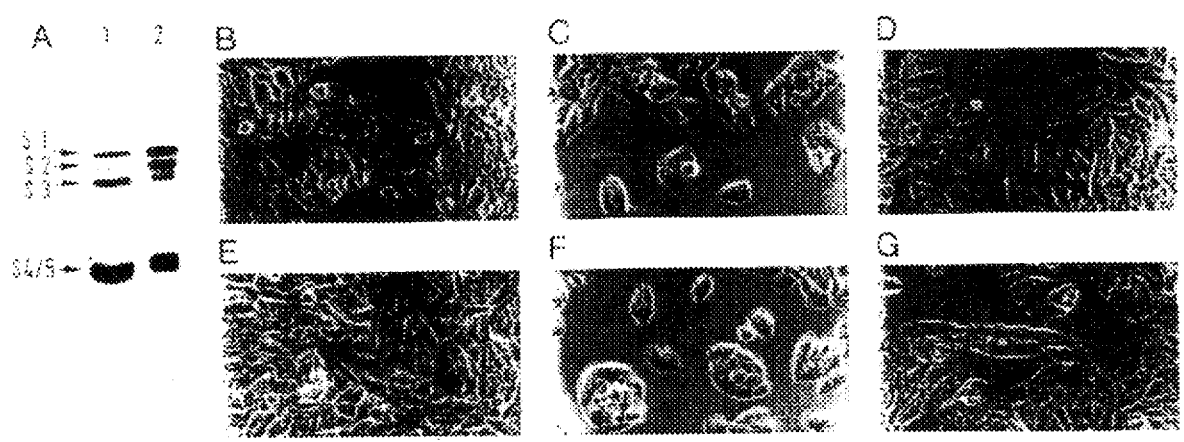

Periplasmic extracts of this strain were subjected to heparin Sepharose CL6B chromatography according to FEMS Microbiol. Lett, 51 (1988) 159–162. When compared with pertussis holotoxin, these preparations contained increased levels of PT sub-units S3 and S4 (FIG. 4 A).

Infect. Immun., 57 (1989) 3324–3330 has shown that the S3-S4 dimer contains a sugar binding receptor. The preponderance of S3 and S4 may reflect binding of the S3-S4 dimer to heparin, a linear glucosaminoglycan (Megret, F., and J. E. Alouf. (1988). A simple novel approach for the purification of pertussis toxin. FEMS Microbiol. Letts. 51:159–162). S1, S2 and S5 were also eluted from the heparin column. Recombinant PT preparations were then assayed for their biological activity using a CHO cell clustering assay. Monoclonal antibody E19, which specifically binds to the S1 sub-unit of PT and inhibits CHO cell clustering by PT, was assayed for inhibition of the morphological change in CHO cells. The tested wild-type pertussis holotoxin and the tested recombinant pertussis holotoxin were adjusted to approximately similar S1 sub-unit concentrations, which was confirmed by comparative Western blot analysis. It was clearly demonstrated (FIG. 4 B and FIG. 4 C) that recombinant PT produces the same morphological effect as PT holotoxin isolated from B. pertussis (FIG. 4 E and FIG. 4 F) and this activity is specifically inhibited by monoclonal antibody E19 (FIG. 4 D and FIG. 4 G). Since PT sub-units are not capable of clustering CHO cells (Bartley, T. D., et al. 1989. Pertussis holotoxoid formed in vitro with a genetically deactivated S1 subunit. Proc. Natl. Acad. Sci. USA. 86:8353–8357; and Burns, D. L., et al. 1987. Role of the A subunit of pertussis toxin in alteration of Chinese hamster ovary cell morphology. Infect. Immun. 55:24–28) this result demonstrates that recombinant pertussis holotoxin (and not just the sub-units) is being formed in the periplasm of B. bronchiseptica ATCC 10580::TnfusPT.

The Figures are explained in more detail below.

FIG. 1 This Figure shows the construction of suicide vectors which contain mini-transposons for PT expression under the control of the tac promoter (pMW126) and are provided for transcriptional fusions with native promoters (pMW127). The PT operon was cloned from plasmid pTX42. The PT genes for sub-units S1 to S5 are represented by open arrows. Plasmids pUT::miniTn5/Km and pUT::T-nPtac contain the IS50$_R$ transposase (tnp; long shaded bar) and 19 base pairs of the terminal Tn5 end (short shaded bars) flanking the kanamycin resistance gene (Kan=Km$^r$; open bar) of pUT::miniTn5/Km and flanking the kanamycin resistance gene, the lactose repressor gene (LacI$^q$), and the tac promoter (P$_{tac}$; filled arrow) of pUT::TnPtac. The terminal Tn5 ends delineate the mini-transposons TnPtacPT (pMW126) and TnfusPT (pMW127). The suicide vehicle pUT also contains a mob site (mob; filled bar) which encodes a conjugal transfer, and the ampicillin resistance gene (Bla; open bar) for selection. The direction of transcription is indicated either by arrows or by the orientation of the open arrows. The features of the plasmids shown are not drawn to scale and only relevant restriction sites are shown.

FIG. 2 This figure shows a Southern hybridization analysis of *B. bronchiseptica* ATCC 10580, which strain contains PT expressing mini-transposons.

A Line 1: Diagram of the PT operon.
A Line 2: Diagram of TnPtacPT
A Line 3: Diagram of TnfusPT The symbols are as described in FIG. 1. Only EcoRI restriction sites are shown.

B: Southern blot (using pMW126 as a probe) of EcoRI digested chromosomal DNA isolated from

| | |
|---|---|
| ATCC 10580 | (lane 1) |
| ATCC 10580::TnPtacPT and | (lane 2) |
| ATCC 10580::TnfuspT | (lane 3). |
| Plasmid pMW126 DNA digested with EcoRI is also shown | (lane 4) |

Molecular weight markers (size in kilobases=kb) and the origin of the reacting bands (see A) are indicated by arrows.

FIG. 3 This Figure shows the results of the analysis of a PT expression by

| | |
|---|---|
| *B. bronchiseptica* ATCC 10580 | (lane 1) |
| containing TnPtacPT | (lane 2) |
| and TnfusPT | (lane 3). |
| *B. pertussis* Tohama | (lane 4) |
| and purified PT are also shown. | (lane 5) |

A: Coomassie stained gel of whole cell extracts.
B: Western blot analysis of whole cell extracts using specific anti-PT monoclonal antibodies E19, E205 and E251. The positions of the PT sub-units S1 to S5 are indicated by arrows.

FIG. 4 Characterization of recombinant PT.

A: Western blot analysis of recombinant PT eluted after heparin Sepharose chromatography of periplasmic extracts from *B. bronchiseptica* ATCC 10580::TnfusPT (lane 1) and purified wild-type PT (lane 2). The positions of the PT sub-units S1 to S5 are indicated by arrows.

B-G: CHO clustering assays without PT (B and E), with recombinant PT (C and D) and with wild-type PT (F and G). Monoclonal antibody E19 is also shown in D and G.

We claim:

1. A plasmid for the stable expression of pertussis toxin in a bacterial microorganism which comprises;

a promoterless hybrid transposon wherein a transposase gene is arranged outside of inverted repeats of the transposon; and having a pertussis toxin operon inserted between the inverted repeats;

said inverted repeats being in shortened form, thereby permitting a further transposition;

said plasmid permitting a stable insertion of the pertussis toxin operon into a bvg-negative bacterial strain.

2. A plasmid according to claim 1 wherein the transposon is a mini-transposon.

3. A plasmid according to claim 1 wherein the transposon is from Tn5 and the inverted repeats each have a length of approximately 19 base pairs.

4. A plasmid according to claim 1 wherein the operon is selected from the group consisting of a wild-type operon and an operon that encodes a pertussis toxin modification effective against whooping cough.

5. A plasmid according to claim 1 wherein the hybrid transposon contains a kanamycin resistance gene.

6. A plasmid which is promotorless having the following features and is a suicide vector that has a mini-transposon for pertussis toxin expression for transcriptional fusions with native promoters, having 1. a mob site,
   2. an ampicillin resistance gene and
   3. in each case, 19 base pairs of the terminal Tn5 end which flank,
   4. a kanamycin resistance gene and
   5. a promotorless operon; and also having
   6. a IS50$_R$-transposase gene.

7. A bvg-negative bacterial strain containing a plasmid according to claim 1.

8. The bacterial strain of claim 7 which is selected from the group consisting of *Bordetella pertussis*, *Bordetella parapertussis* and *Bordetella bronchiseptica*.

9. A bvg-negative bacterial strain wherein a pertussis toxin operon has been incorporated by means of a plasmid according to one of claims 1, 2 and 3 to 6.

10. The strain of claim 9 selected from the group of species consisting of *Bordetella pertussis*, *Bordetella parapertussis* and *Bordetella bronchiseptica*.

11. The strain of claim 10 which is *Bordetella bronchiseptica* ATCC 10580.

12. A process for the stable expression of pertussis toxin which comprises;

culturing a bvg-negative bacterial strain containing a plasmid according to one of claims 1, 2 and 3 to 6.

* * * * *